US008727998B2

(12) United States Patent
Yin et al.

(10) Patent No.: US 8,727,998 B2
(45) Date of Patent: May 20, 2014

(54) PORTAL VEIN PRESSURE MEASUREMENT USING ELASTOGRAPHY

(75) Inventors: Meng Yin, Rochester, MN (US); Jayant A. Talwalkar, Rochester, MN (US); Anthony J. Romano, Washington, D.C., DC (US); Armando Manduca, Rochester, MN (US); Richard L. Ehman, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 1008 days.

(21) Appl. No.: 12/599,721

(22) PCT Filed: May 15, 2008

(86) PCT No.: PCT/US2008/063709
§ 371 (c)(1),
(2), (4) Date: Nov. 11, 2009

(87) PCT Pub. No.: WO2008/144391
PCT Pub. Date: Nov. 27, 2008

(65) Prior Publication Data
US 2010/0241012 A1    Sep. 23, 2010

Related U.S. Application Data

(60) Provisional application No. 60/930,397, filed on May 16, 2007.

(51) Int. Cl.
*A61B 5/02*    (2006.01)

(52) U.S. Cl.
USPC .......................................................... 600/485

(58) Field of Classification Search
USPC .......................................................... 600/485
See application file for complete search history.

(56) References Cited

U.S. PATENT DOCUMENTS

| 5,592,085 A | 1/1997 | Ehman |
| 7,034,534 B2 | 4/2006 | Ehman et al. |
| 2007/0016031 A1* | 1/2007 | Mourad et al. ................. 600/437 |

OTHER PUBLICATIONS

Garra, "Imaging of Tissue Elasticity: Will it Become an Important Clinical Tool?" Proc. Fifth Int'l. Conf. Ultrasonic Meas. and Imag. of Tissue Elasticity, p. 26; Oct. 8-11, 2006.*

Deffieux, et al. "Ultrafast Ultrasonic Imaging Applied to Measurements of in Vivo Muscle Contraction Features" Proc. Fifth Int'l. Conf. Ultrasonic Meas. and Imag. of Tissue Elasticity, p. 103; Oct. 8-11, 2006.*

Righetti, et al. Image Quality Issues in Poroelastographyo Proc. Fifth Int'l. Conf. Ultrasonic Meas. and Imag. of Tissue Elasticity; p. 46; Oct. 8-11, 2006.*

(Continued)

*Primary Examiner* — Michael Kahelin
*Assistant Examiner* — Mitchell Alter
(74) *Attorney, Agent, or Firm* — Quarles & Brady, LLP

(57) ABSTRACT

The shear stiffness of a subject's spleen is measured using elastography techniques such as ultrasound elastography or a magnetic resonance elastography (MRE) acquisition with an MRI system. A relationship between splenic shear stiffness and portal venous blood pressure is modeled and is used to calculate portal venous blood pressure non-invasively from the measured splenic shear stiffness.

22 Claims, 5 Drawing Sheets

(56) References Cited

OTHER PUBLICATIONS

Weaver, et al. "Magnetic Resonance Elastography using 3D Gradient Echo Measurements of Steady-State Motion" 0 Med. Phys. vol. 28, No. 8; p. 1620-1628 (2001).*

Deng, et al., "Splenorenal Reflex Regulation of Arterial Pressure", Hypertension, 2001; 38: 348-352.*

The International Search Report and Written Opinion as mailed on Sep. 22, 2008 for International Patent Application PCT/US2008/063709.

Weaver, et al. "Magnetic Resonance Elastography using 3D Gradient Echo Measurements of Steady-State Motion" Med. Phys. vol. 28, No. 8; p. 1620-1628 (2001). Abstract; p. 1621, col. 1, para 4.

Righetti, et al. "Image Quality Issues in Poroelastography" Proc. Fifth Int'l. Conf. Ultrasonic Meas. and Imag. of Tissue Elasticity; p. 46; Oct. 8-11, 2006.

Manduca, et al., Magnetic resonance elstrography: Non-invasive mapping of tissue elasticity—Medical Image Analysis, vol. 5(4), 2001, pp. 237-254.

* cited by examiner

PORTAL VEIN PRESSURE MEASUREMENT USING ELASTOGRAPHY

CROSS-REFERENCE TO RELATED APPLICATIONS

This application claims priority to PCT International Application No. PCT/US2008/063709 filed on May 15, 2008, which claims priority to U.S. Provisional Patent Application No. 60/930,397 filed on May 16, 2007, incorporated by reference herein.

STATEMENT REGARDING FEDERALLY SPONSORED RESEARCH

This invention was made with government support under Grant No. EB001981 awarded by the National Institute of Biomedical Imaging and Bioengineering. The United States Government has certain rights in this invention.

BACKGROUND OF THE INVENTION

The field of the invention is the non-invasive determination of tissue elasticity with medical imaging techniques, such as ultrasound or magnetic resonance elastography imaging.

The physician has many diagnostic tools at his or her disposal which enable detection and localization of diseased tissues. These include x-ray systems that measure and produce images indicative of the x-ray attenuation of the tissues and ultrasound systems that detect and produce images indicative of tissue echogenicity and the boundaries between structures of differing acoustic properties. Nuclear medicine produces images indicative of those tissues which absorb tracers injected into the patient, as do PET scanners and SPECT scanners. And finally, magnetic resonance imaging ("MRI") systems produce images indicative of the magnetic properties of tissues. It is fortuitous that many diseased tissues are detected by the physical properties measured by these imaging modalities, but it should not be surprising that many diseases go undetected.

Elastography is a technique for quantitatively assessing the mechanical properties (e.g., stiffness) of soft tissues. In the most common embodiment, it includes measuring the displacement of tissue in response to an applied force or stress, and using that information to determine the stiffness of the material. The applied stress can be static, quasi-static, transient, or dynamic (with the most common dynamic case being harmonic motion). Techniques for using MRI or ultrasound to perform elastography are well known.

In most vessels in the body, blood pressure can be measured either externally or internally via a catheter. However, the portal vein, the principal blood supply to the liver, lies deep within the body and has capillary beds on both sides that make it difficult to reach by catheter. Portal venous hypertension (PVH) is one of the most important consequences of chronic liver disease, leading to gastroesophageal varices and potential life-threatening hemorrhagic complications.

Currently, portal venous pressure is assessed by hepatic vein catheterization and measurement of hepatic venous "wedge pressure". Unfortunately, the highly invasive nature of this procedure severely limits the potential to use portal pressure data to guide clinical management. Conventional MRI and CT can only diagnose PVH by detecting late consequences of portal vein hypertension such as varices, splenomegaly and ascites. Thus, although portal pressure is considered an important indicator of various disease processes, it is currently very difficult to measure.

Previous studies with both ultrasound and MR elastography have established that there is a strong relationship between increasing liver stiffness and the severity of hepatic fibrosis. It is also know that portal venous pressure increases systematically with the severity of liver fibrosis.

SUMMARY OF THE INVENTION

The present invention is a method for measuring portal venous blood pressure by measuring the stiffness of the spleen using an elastography technique. The spleen is connected to the portal vein, and can be thought of as a sponge filled with blood, whose stiffness should vary with blood pressure. Increased portal blood pressure should thus translate to increased splenic stiffness. Accordingly, splenic stiffness is measured by elastography and this stiffness measurement is converted to a portal vein blood pressure measurement to enable a simple yet clinical important non-invasive assessment of portal pressure.

To translate splenic stiffness to pressure, a mathematical model has been developed. An initial simple approach outlined below assumes that splenic stiffness changes with portal vein pressure as an ideal fluid, and that the Poisson ratio of the splenic material remains constant. This model also implicitly assumes that the spleen behaves uniformly across patients.

The equation of state for an ideal fluid can be expressed as $P = -\beta \vec{\nabla} \cdot \vec{s}$, where P is the pressure, $\beta$ is the bulk modulus and $\vec{\nabla} \cdot \vec{s}$ is the divergence of the displacement s. For a one-dimensional wave, we obtain $P = k\beta s$. Define the wavenumber k as $\omega/c$, where $\omega$ is the radial frequency and c the velocity of longitudinal propagation $c = \sqrt{\beta/\rho}$, where $\rho$ is the density of the medium. Then the previous equation can be reduced to the expression $P = \sqrt{\beta} \cdot \sqrt{\rho} \omega s$.

For a particular calibration or baseline measurement, consider the expression $$\frac{P_0}{\sqrt{\beta_0}} = \sqrt{\rho_0} \cdot \omega_0 \cdot s_0$$

where the subscripts "0" imply a baseline measurement. If a second measurement is performed in which the pressure and bulk modulus vary, yet in which the baseline density, radial frequency, and displacement amplitude remain constant, we may obtain the equality $$\frac{P}{\sqrt{\beta}} = \frac{P_0}{\sqrt{\beta_0}}$$

and rearranging the equation yields $$P(\beta) = P_0 \sqrt{\frac{\beta}{\beta_0}}.$$

Therefore, if the baseline pressure $P_0$ and bulk modulus $\beta_0$ can be known, and the current bulk modulus $\beta$ can be measured, the corresponding pressure $P(\beta)$ can be predicted. Consider now the relationship between bulk modulus $\beta$ and shear modulus $\mu$ which can be expressed as $$\beta = \mu \cdot \frac{2(1+v)}{1-2v}$$

where v is Poisson's ratio. If Poisson's ratio can be assumed to be a constant between measurements, then substitution yields $$P(\mu) = P_0 \sqrt{\frac{\mu}{\mu_0}}$$

This final expression provides a relationship between a baseline calibration measurement for postal venous blood pressure and shear modulus, the current measured shear modulus, and the corresponding predicted blood pressure.

FIG. 3 shows the dependence of portal vein blood pressure on measured shear modulus, using a baseline calibration of 3 kPa for normal spleen at a normal portal vein blood pressure of 3 mmHg. This indicates that changes in splenic stiffness in patients with hepatic fibrosis reflect the degree of portal venous hypertension. More sophisticated models may be used to more closely model the poroelastic behavior of the spleen, and possible changes in the Poisson ratio with portal venous blood pressure.

DETAILED DESCRIPTION OF THE PREFERRED EMBODIMENT

Figure 1:
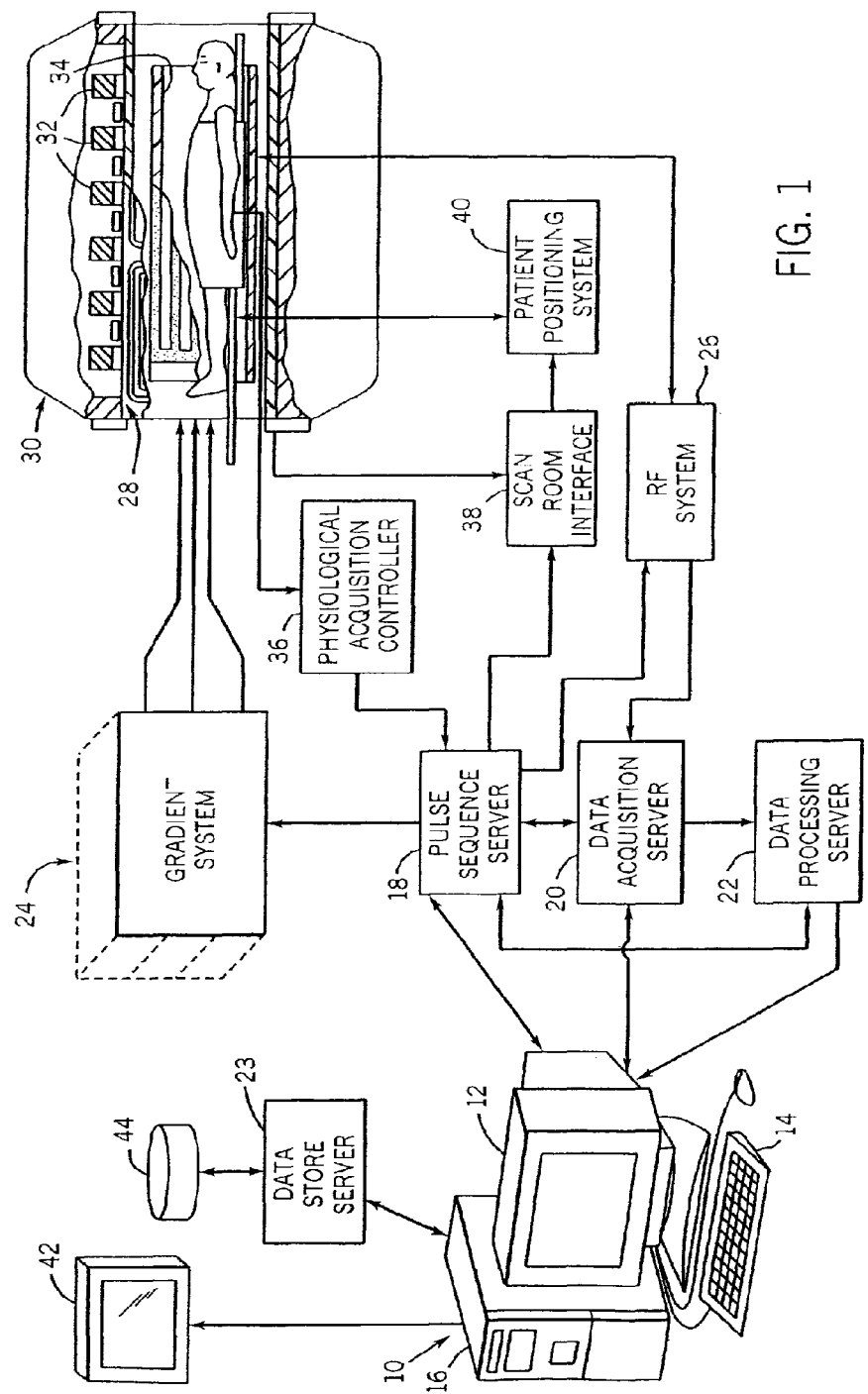
FIG. 1 is a block diagram of a preferred MRI system which is used to practice the present invention.

As described below, the present invention can be utilized with MR elastography (MRE) by using harmonic mechanical excitation with an acoustic driver and a 2D gradient recalled echo pulse sequence. However, other types of mechanical drivers, pulse sequences, and types of excitation are also possible. Additionally, the present invention is readily applicable to other systems for performing elastography studies, such as using ultrasound techniques to measure the tissue displacements induced by the mechanical drivers.

Any nucleus which possesses a magnetic moment attempts to align itself with the direction of the magnetic field in which it is located. In doing so, however, the nucleus precesses around this direction at a characteristic angular frequency (Larmor frequency) which is dependent on the strength of the magnetic field and on the properties of the specific nuclear species (the magnetogyric constant γ of the nucleus). Nuclei which exhibit this phenomena are referred to herein as "spins", and materials which contain such nuclei are referred to herein as "gyromagnetic".

When a substance such as human tissue is subjected to a uniform magnetic field (polarizing field B0), the individual magnetic moments of the spins in the tissue attempt to align with this polarizing field, but precess about it in random order at their characteristic Larmor frequency. A net magnetic moment Mz is produced in the direction of the polarizing field, but the randomly oriented magnetic components in the perpendicular, or transverse, plane (x-y plane) cancel one another. If, however, the substance, or tissue, is subjected to a magnetic field (excitation field B1) which is in the x-y plane and which is near the Larmor frequency, the net aligned moment, Mz, may be rotated, or "tipped", into the x-y plane to produce a net transverse magnetic moment Mt, which is rotating, or spinning, in the x-y plane at the Larmor frequency. The practical value of this phenomenon resides in the signal which is emitted by the excited spins after the excitation signal B1 is terminated. There are a wide variety of measurement sequences in which this nuclear magnetic resonance ("NMR") phenomenon is exploited.

When utilizing NMR to produce images, a technique is employed to obtain NMR signals from specific locations in the subject. Typically, the region which is to be imaged (region of interest) is scanned by a sequence of NMR measurement cycles which vary according to the particular localization method being used. The resulting set of received NMR signals are digitized and processed to reconstruct the image using one of many well known reconstruction techniques. To perform such a scan, it is, of course, necessary to elicit NMR signals from specific locations in the subject. This is accomplished by employing magnetic fields (Gx, Gy, and Gz) which are superimposed on the polarizing field B0, but which have a gradient along the respective x, y and z axes. By controlling the strength of these gradients during each NMR cycle, the spatial distribution of spin excitation can be controlled and the location of the resulting NMR signals can be identified.

It has been found that MR imaging can be enhanced when an oscillating stress is applied to the object being imaged in a method called MR elastography (MRE). The method requires that the oscillating stress produce shear waves that propagate through the organ, or tissues to be imaged. When magnetic gradients oscillating at the same frequency as the shear wave are present, these shear waves alter the phase of the NMR signals, and from this the mechanical properties of the subject can be determined. In many applications, the production of shear waves in the tissues is merely a matter of physically vibrating the surface of the subject with an electromechanical device such as that disclosed in above-cited U.S. Pat. No. 5,592,085. For example shear waves may be produced in the breast and prostate by direct contact with the oscillatory device. Also, with organs like the liver, the oscillatory force can be applied by means of an applicator, such as that described in U.S. Pat. No. 7,034,534, the disclosure of which is incorporated herein by reference.

Referring now to FIG. 1, the preferred embodiment of the invention is employed in an MRI system. The MRI system includes a workstation 10 having a display 12 and a keyboard 14. The workstation 10 includes a processor 16 which is a commercially available programmable machine running a commercially available operating system. The workstation 10 provides the operator interface which enables scan prescriptions to be entered into the MRI system.

The workstation 10 is coupled to four servers: a pulse sequence server 18; a data acquisition server 20; a data processing server 22, and a data store server 23. In the preferred embodiment the data store server 23 is performed by the workstation processor 16 and associated disc drive interface circuitry. The remaining three servers 18, 20 and 22 are performed by separate processors mounted in a single enclosure and interconnected using a 64-bit backplane bus. The pulse sequence server 18 employs a commercially available microprocessor and a commercially available quad communication controller. The data acquisition server 20 and data processing server 22 both employ the same commercially available microprocessor and the data processing server 22 further includes one or more array processors based on commercially available parallel vector processors.

The workstation 10 and each processor for the servers 18, 20 and 22 are connected to a serial communications network.

This serial network conveys data that is downloaded to the servers 18, 20 and 22 from the workstation 10 and it conveys tag data that is communicated between the servers and between the workstation and the servers. In addition, a high speed data link is provided between the data processing server 22 and the workstation 10 in order to convey image data to the data store server 23.

The pulse sequence server 18 functions in response to program elements downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$, and $G_z$ used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2+Q^2},$$

and the phase of the received NMR signal may also be determined:

$$\phi=\tan^{-1} Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

It should be apparent that the pulse sequence server 18 performs real-time control of MRI system elements during a scan. As a result, it is necessary that its hardware elements be operated with program instructions that are executed in a timely manner by run-time programs. The description components for a scan prescription are downloaded from the workstation 10 in the form of objects. The pulse sequence server 18 contains programs which receive these objects and converts them to objects that are employed by the run-time programs.

The digitized NMR signal samples produced by the RF system 26 are received by the data acquisition server 20. The data acquisition server 20 operates in response to description components downloaded from the workstation 10 to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information which is used to control the scan.

The data processing server 22 receives NMR data from the data acquisition server 20 and processes it in accordance with description components downloaded from the workstation 10. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 which is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 5:
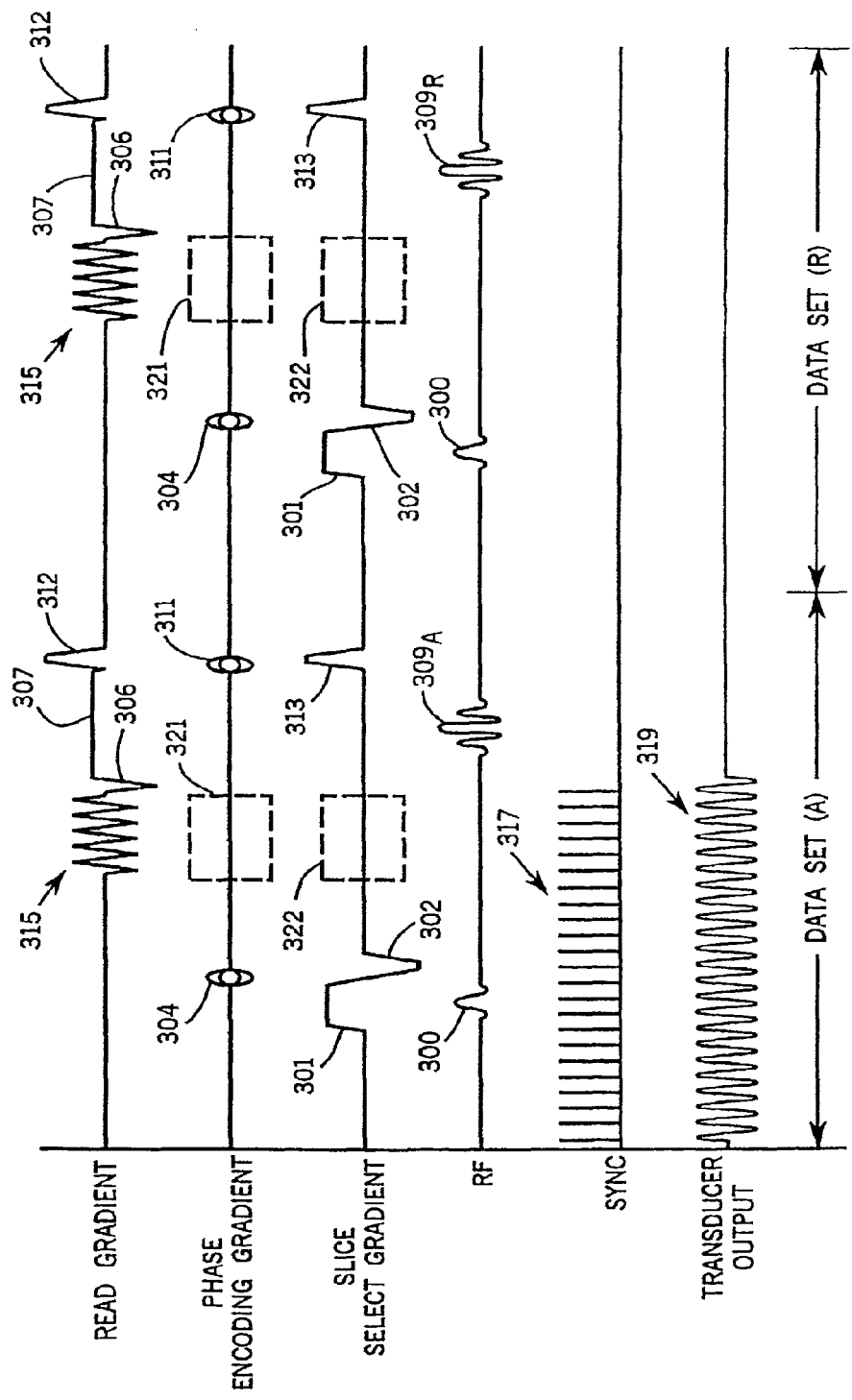
FIG. 5 is a graphic representation of an MRE pulse sequence used to direct the operation of the MRI system of FIG. 1.

Referring particularly to FIG. 5, a preferred embodiment of a pulse sequence which may be used to acquire NMR data is shown. Actually, two pulse sequences are shown, with the first being used to acquire NMR data for a synchronous spin motion image (A), and the second being used to acquire NMR data for a reference image (R). In the preferred embodiment, these two pulse sequences are alternated throughout the scan such that the corresponding views (i.e. phase encodings) in the data sets (A) and (R) are acquired at substantially the same moment in time.

The pulse sequences are fundamentally a 2DFT pulse sequence using a gradient recalled echo. Transverse magnetization is produced by a selective 90° RF excitation pulse 300 which is produced in the presence of a slice select gradient ($G_z$) pulse 301 and followed by a rephasing gradient pulse 302. A phase encoding gradient ($G_y$) pulse 304 is then applied at an amplitude and polarity determined by the view number of the acquisition. A read gradient ($G_x$) is applied as a negative dephasing lobe 306, followed by a positive readout gradient pulse 307. An NMR echo signal 309 is acquired 40 msecs. after the RF excitation pulse 300 during the readout pulse 307 to frequency encode the 256 digitized samples. The pulse sequence is concluded with spoiler gradient pulses 312 and 313 along read and slice select axes, and a rephasing gradient pulse 311 is applied along the phase encoding axis ($G_y$). As is well known in the art, this rephasing pulse 311 has the same size and shape, but opposite polarity of the phase encoding pulse 304. The pair of pulse sequences are repeated 64 times with the phase encoding pulse 304 stepped through its successive values to acquire a 64 by 256 array of complex NMR signal samples that comprise the data set (A) and a 64 by 256 array of complex NMR signal samples that comprise the reference data set (R).

An alternating magnetic field gradient is applied after the transverse magnetization is produced and before the MRE signal is acquired. In the preferred embodiment illustrated in FIG. 5, the read gradient ($G_x$) is used for this function and is alternated in polarity to produce five bipolar, gradient waveforms 315. The alternating gradient 315 has a frequency of 60 Hz. At the same time, the pulse generator module 121 produces sync pulses as shown at 317, which are also at a frequency of 60 Hz and have a specific phase relationship with the alternating gradient pulses 315. As explained below, these sync pulses 317 activate a transducer to apply an oscillating stress indicated at 319 to the patient which has the same frequency and phase relationship. To insure that the resulting waves have time to propagate throughout the field of view, the sync pulses 317 may be turned on well before the pulse sequence begins, as shown in FIG. 5.

The reference pulse sequence is designed to measure the signal phase produced by sources other than synchronized spin movement. This is accomplished by repeating the identical pulse sequence, but without applying the oscillating stress 319. As a result, the phase of the acquired NMR signal $309_R$ will be affected by "static" system phase errors caused by field inhomogeneities and the like as well as the phase due to random spin movement along the x-axis. However, there will not be a phase component due to synchronous spin movement and the reference phase $\phi_R$ can, therefore, be subtracted from the phase $\phi_A$ to yield the phase ($\phi$) due solely to synchronous spin motion.

The pulse sequence in FIG. 5 can be modified to measure synchronous spin movement along the other gradient axes (y and z). For example, the alternating magnetic field gradient pulses may be applied along the phase encoding axis (y) as indicated by dashed lines 321, or they may be applied along the slice select axis (z) as indicated by dashed lines 322. Indeed, they may be applied simultaneously to two or three of the gradient field directions to "read" synchronous spin movements along any desired direction.

Phase sensitivity to synchronous motion can also be increased by applying both the alternating gradient pulses 315 and the sync pulses 317 during the reference pulse sequence. However, when this is done the phase of the alternating magnetic field gradient 315 must be inverted 180° relative to the sync pulses 317 so that the sign of the accumulated phase is reversed. In addition, the magnetic field gradients are flow compensated as described, for example, in U.S. Pat. No. 4,728,890 by Pattany et al., which is hereby incorporated by reference. Such flow compensation removes any phase component due to random spin motion without significantly affecting the sensitivity to synchronous spin motion. Consequently, when the phase difference image is produced the phase accumulations due to synchronous spin motion add together, while phase accumulations due to other sources subtract and are thereby nulled.

The pulse sequence of FIG. 5 directs the MRI system of FIG. 1 to collect axial wave images with the following pulse sequence parameters:
FOV=32 to 42 cm,
Flip angle=30°,
Slice thickness=10 mm
TR=50 msecs.,
TE=32 msecs.

The pair of phase images $Q_A$ and $Q_R$ are acquired with through-plane motion encoding gradients and these are acquired at 4 phase offsets. Several imaging planes containing much of the liver and spleen are acquired.

The physical properties of tissue are measured using MR elastography by applying a stress (e.g., tension, pressure, or shear) and observing the resulting strain (e.g., elongation, compression, rotation). By measuring the resulting strain, elastic properties of the tissue such as Young's modulus, Poisson's ratio, the shear modulus and the bulk modulus, can be calculated. By applying the stress and measuring the resulting strain, the elastic properties of the tissue can be completely defined as described in U.S. Pat. No. 5,592,085. By observing the rate at which the strain decreases as a function of distance from the stress producing source, the attenuation of the strain wave can be estimated. From this, the viscous properties of the gyromagnetic medium may be estimated. The dispersion characteristics of the medium can be estimated by observing the speed and attenuation of the strain waves as a function of their frequency.

Figure 2:
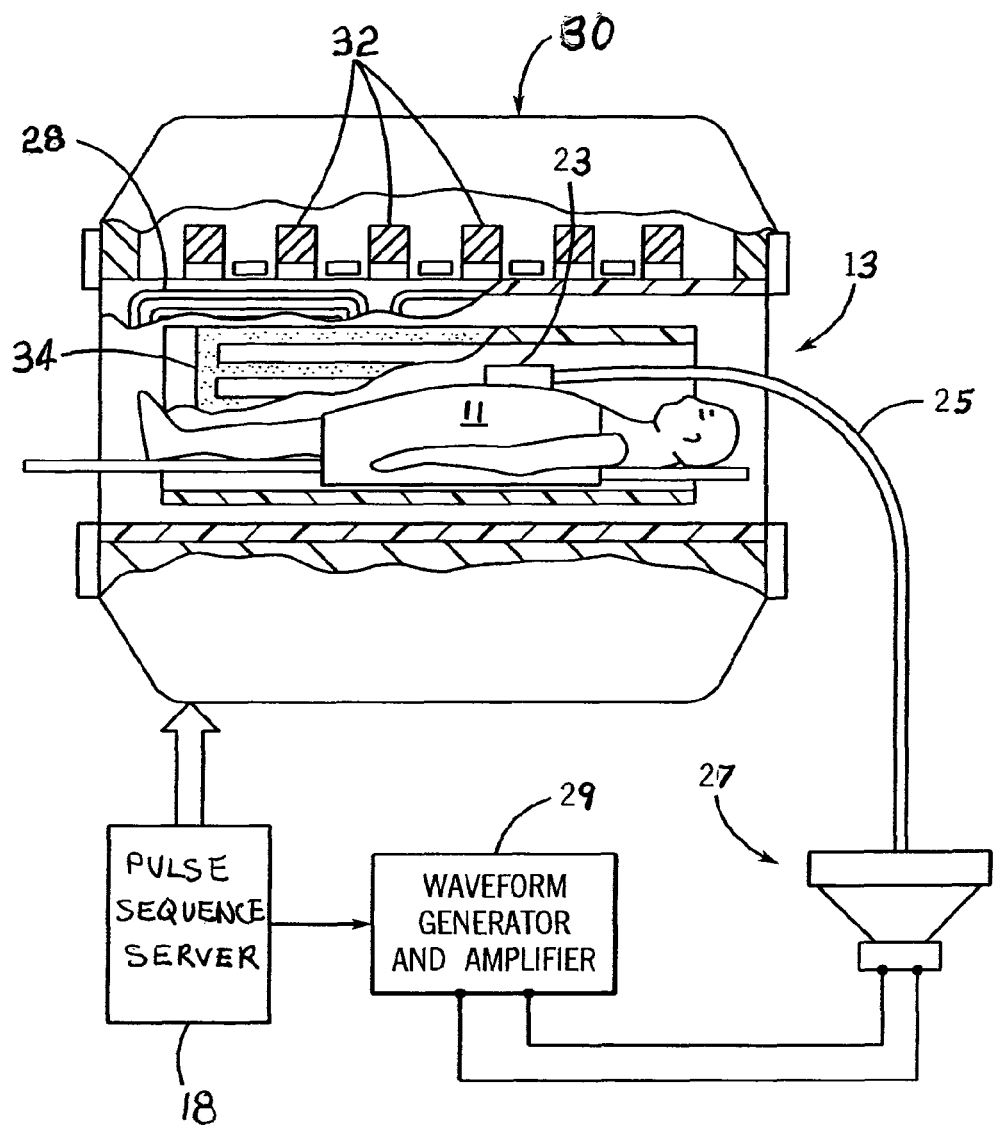
FIG. 2 is a pictorial representation of a driver system used with the MRI system of FIG. 1 to control an MRE scan of the subject's spleen.

Referring particularly to FIG. 2, a subject to be examined 11 is placed in the bore 13 of the MRI system magnet 30 and is subjected to magnetic fields produced by polarizing coil 32, gradient coils 28 and an RF coil 34 during the acquisition of NMR data from the splenic region in the subject 11. An MRE driver is placed on the subject 11 and energized to produce an oscillating stress. It includes a passive actuator 23 which is positioned anterior to the subject's spleen and is connected by means of a tube 25 to a remotely located acoustic driver assembly 27. The acoustic driver assembly 27 is remote from the bore 13 of the magnet 30 in the sense that it is away from the strong magnetic field produced by the magnet 30 where its operation is not impeded by those fields, and where its operation will not perturb the MRI system magnetic fields. The acoustic driver assembly 27 is electrically driven by a waveform generator and amplifier 29, which in turn is controlled by the pulse sequencer 18 in the MRI system. The MRI pulse sequencer 18 directs the MRI system to perform an MRE pulse sequencer 18 scan as described above, while enabling the waveform generator 29 at the proper moment during each pulse sequence to apply an oscillatory stress to the subject 11.

The acoustic driver assembly 27 includes a loudspeaker driver that directs acoustic energy into an enclosure. One end of the tube 25 connects to the enclosure and is acoustically coupled to its interior. As a result, the acoustic energy produced by the loudspeaker is directly coupled to one end of the tube 25 and conveyed from the driver assembly 27 to the passive actuator 23.

The passive actuator 23 is comprised of a cylindrical shaped enclosure having a diameter of 19 cm connected to the end of tube 24. The enclosure is formed by a rigid, cylindrical outer wall and a rigid circular end wall that connects to an end of the outer wall 52. An input hole is formed in the outer wall or end wall to acoustically couple the tube 25 to the interior chamber of the enclosure. The rigid walls are made of a polycarbonate or other non-ferrous, non-electrically conducting material which is both rigid and relatively "invisible" to the magnetic fields produced in the bore of the magnet.

Stretched across the other end of the cylindrical outer wall is a flexible membrane. The membrane can be made of rubber or any sufficiently elastic material. This flexible membrane rests against the surface of the subject 11 and vibrates in response to the acoustic energy received through the tube 25. The vibrations apply an oscillating stress to the subject's skin which is conveyed into the liver and spleen.

Figure 3:
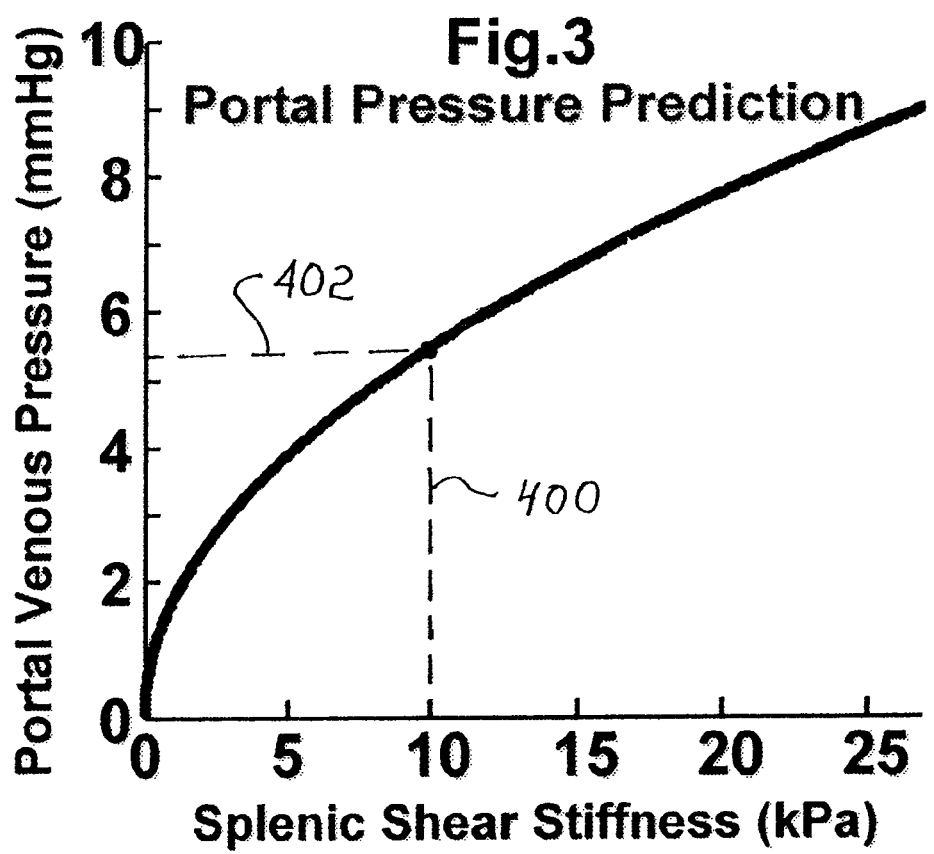
FIG. 3 is a graphic representation of the relationship between spleen stiffness and portal venous blood pressure.

A scan is conducted as described above using the pulse sequence of FIG. 5 and the acoustic driver of FIG. 2. Stiffness images are reconstructed by reconstructing the phase images described above and using a local frequency estimator (LFE) inversion method or direct inversion (DI) method, as described by A. Manduca, Med. Image Anal. 2001, 5(4):237-254, or other alternative inversion techniques, to produce a shear stiffness image of the spleen. A shear stiffness value for the spleen is calculated from this image by averaging stiffness values within a region of interest within the spleen. The portal venous pressure is calculated from this splenic shear stiffness using the model relationship depicted in FIG. 3 or a similar relationship from a more sophisticated model. For example, if the measured splenic shear stiffness in kPa is 10, as indicated by dashed line 400, then the portal venous pressure in mmHg is 5.3 as indicated by dashed line 402. MRE demonstrates changes in splenic stiffness in patients with hepatic fibrosis that reflects the degree of portal venous hypertension. Our model relating splenic stiffness to portal pressure provides an MRE measurement of splenic stiffness which may be employed to estimate changes in portal venous pressure in response to therapy.

Figure 4:
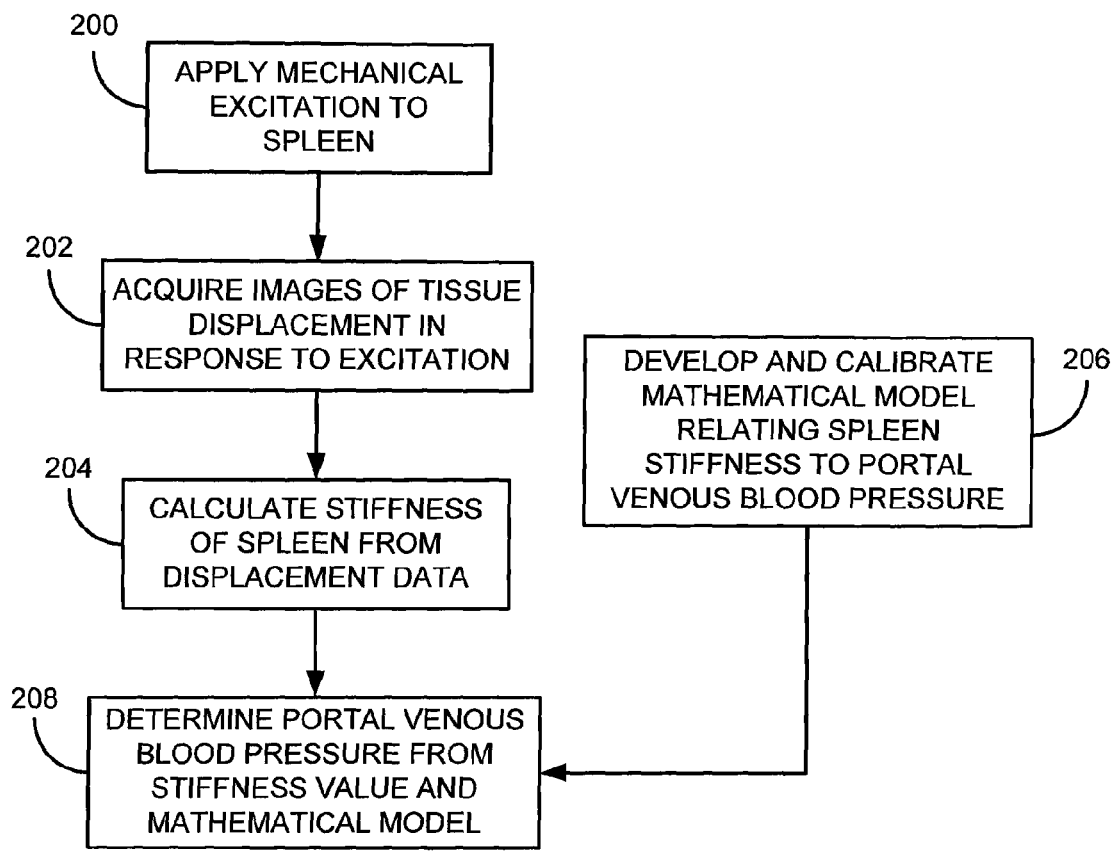
FIG. 4 is a flow chart setting forth the steps of a method in accordance with the invention.

The above described process is further illustrated with respect to FIG. 4. In particular, at process block 200 a mechanical excitation is applied to the tissue of interest. The mechanical excitation can be performed in a number of different ways or combinations thereof. For example, it may be performed using with an active or passive acoustic driver, an electromechanical driver, a piezoelectric driver, or focused ultrasound. The excitations may be a harmonic or a combination of harmonic mechanical excitations to the spleen, a transient mechanical excitation to the spleen static mechanical excitation, or quasi-static mechanical excitation.

The process continues at process block 202 by imaging the displacement of tissue in response to this excitation. As described, it is contemplated that a variety of imaging modalities may be utilized, such as ultrasound and MRI. Thereafter, the stiffness of the material is calculated at process block 204 using the data acquired using the imaging modality.

In addition to data acquisition and stiffness calculations, a mathematical model to relate spleen stiffness to portal venous blood pressure, such as the model described above, is developed at process block 206. At process block 208, the calculated splenic stiffness is entered into the mathematical model and the model's prediction of portal venous blood pressure is calculated.

The present invention has been described in terms of the various embodiments, and it should be appreciated that many equivalents, alternatives, variations, and modifications, aside from those expressly stated, are possible and within the scope of the invention. Therefore, the invention should not be limited to a particular described embodiment.

The invention claimed is:

1. A method for measuring portal venous blood pressure in a subject, the method comprising the steps of:
    a) applying a mechanical excitation to spleen of the subject;
    b) acquiring displacement data relating to tissue displacement in the spleen in response to this applied force with a medical imaging system;
    c) calculating a splenic shear stiffness value from the acquired displacement data;
    d) developing a mathematic model between splenic shear stiffness and portal venous blood pressure; and
    e) calculating the portal venous blood pressure using the calculated splenic shear stiffness value and the mathematic model between splenic shear stiffness and portal venous blood pressure.

2. The method as recited in claim 1 wherein step a) further includes applying the mechanical excitation to the spleen with an active or passive acoustic driver.

3. The method as recited in claim 1 wherein step a) further includes applying mechanical excitation to the spleen with an electromechanical driver.

4. The method as recited in claim 1 wherein step a) further includes applying mechanical excitation to the spleen with a piezoelectric driver.

5. The method as recited in claim 1 wherein step a) further includes applying mechanical excitation to the spleen with focused ultrasound.

6. The method as recited in claim 1 wherein step a) further includes applying one of a harmonic and a combination of harmonic mechanical excitations to the spleen.

7. The method as recited in claim 1 wherein step a) further includes applying transient mechanical excitation to the spleen.

8. The method as recited in claim 1 wherein step a) further includes applying one of static and quasi-static mechanical excitation to the spleen.

9. The method as recited in claim 1 wherein step b) includes performing an ultrasound imaging process to acquire the displacement data from the spleen.

10. The method as recited in claim 1 wherein step b) includes performing a magnetic resonance (MR) imaging process to acquire the displacement data from the spleen.

11. The method as recited in claim 10 wherein step b) includes performing phase contrast magnetic resonance techniques to encode the displacement in the subject's spleen as changes in the phase of an MR signal.

12. The method as recited in claim 11 wherein step b) includes performing a gradient recalled echo pulse sequence to acquire the displacement data from the spleen.

13. The method as recited in claim 11 wherein step b) includes performing a spin echo pulse sequence to acquire the displacement data from the spleen.

14. The method as recited in claim 11 wherein step b) includes performing an echo planar imaging pulse sequence to acquire the displacement data from the spleen.

15. The method as recited in claim 11 wherein step b) includes performing a steady state free precession pulse sequence to acquire the displacement data from the spleen.

16. The method as recited in claim 11 wherein step b) includes acquiring data in at least one 2D imaging slice.

17. The method as recited in claim 11 wherein step b) includes acquiring data in a 3D imaging volume.

18. The method as recited in claim 1 wherein step a) further includes applying at least one of a harmonic, a combination of harmonics, and transient mechanical excitation to the spleen and wherein step c) includes estimating the shear stiffness of the spleen based on inversions of the equations of acoustic wave propagation in materials.

19. The method as recited in claim 1 wherein step a) further includes applying at least one of a harmonic, a combination of harmonics, and transient mechanical excitation to the spleen and wherein step c) includes estimating the shear stiffness of the spleen based on an estimation of one of the shear wave speed and wavelength.

20. A method for measuring portal venous blood pressure in a subject, the method comprising the steps of:
   a) applying a mechanical excitation to spleen of the subject;
   b) acquiring displacement data relating to tissue displacement in the spleen in response to this applied force with a medical imaging system;
   c) calculating a splenic shear stiffness value from the acquired displacement data;
   d) developing a mathematic model between splenic shear stiffness and portal venous blood pressure;
   e) calculating the portal venous blood pressure using the calculated splenic shear stiffness value and the mathematic model between splenic shear stiffness and portal venous blood pressure; and
   wherein step e) further includes converting the measured shear stiffness of the spleen to an estimate of portal venous blood pressure based on a model that assumes that splenic stiffness changes with portal vein pressure as an ideal fluid, that the Poisson ratio of the splenic material remains constant, and that the spleen behaves uniformly across patients.

21. A method for measuring portal venous blood pressure in a subject, the method comprising the steps of:
   a) applying a mechanical excitation to spleen of the subject;
   b) acquiring displacement data relating to tissue displacement in the spleen in response to this applied force with a medical imaging system;
   c) calculating a splenic shear stiffness value from the acquired displacement data;
   d) developing a mathematic model between splenic shear stiffness and portal venous blood pressure;
   e) calculating the portal venous blood pressure using the calculated splenic shear stiffness value and the mathematic model between splenic shear stiffness and portal venous blood pressure; and
   wherein step e) further includes converting the measured shear stiffness of the spleen to an estimate of portal venous blood pressure based on a model that takes into account the poroelastic behavior of the spleen.

22. The method as recited in claim 1 wherein the mathematic model is $$P(\mu) = P_0 \sqrt{\frac{\mu}{\mu_0}},$$

wherein $P(\mu)$ is the postal venous blood pressure, $\mu$ is the splenic shear modulus, $\mu_0$ is the base-line calibration measurement for splenic shear modulus and $P_0$ is the base-line calibration measurement for postal venous blood pressure.

* * * * *